United States Patent [19]
de Bold

[11] Patent Number: 4,761,469
[45] Date of Patent: Aug. 2, 1988

[54] ISOLATION, PURIFICATION AND SEQUENCE DETERMINATION OF CARDIONATRINS

[75] Inventor: Adolfo J. de Bold, Kingston, Canada

[73] Assignee: Queen's University at Kingston, Kingston, Canada

[21] Appl. No.: 15,514

[22] Filed: Feb. 13, 1987

Related U.S. Application Data

[63] Continuation of Ser. No. 706,379, Feb. 27, 1985, abandoned, which is a continuation-in-part of Ser. No. 546,817, Oct. 31, 1983, Pat. No. 4,663,437, Ser. No. 473,442, Mar. 9, 1983, abandoned, and Ser. No. 351,036, Feb. 22, 1982, abandoned, said Ser. No. 546,817, is a continuation-in-part of Ser. No. 473,442, , which is a continuation-in-part of Ser. No. 351,036.

[51] Int. Cl.$^4$ .............................................. C07K 7/10
[52] U.S. Cl. .................................................... 530/324
[58] Field of Search ......................................... 530/324

[56] References Cited

U.S. PATENT DOCUMENTS 4,508,712  4/1985  Needleman .................. 260/112.5 R

OTHER PUBLICATIONS

Vol. 167, No. 2, FEBS 1268, Feb. 1984, pp. 352-357.

Primary Examiner—Delbert R. Phillips
Attorney, Agent, or Firm—Richard J. Hicks

[57] ABSTRACT

Four peptides have been isolated from mammalian atria which exhibit potent diuretic, natiuretic and vasodilatory properties. These peptides derive from a common precursor preprocardionatrin of 152 amino acids in a determined sequence. Cardionatrin III and IV, having molecular weights of about 8,000 and 13,700 respectively have been isolated, purified by chromatographic techniques and their amino acid sequence determined.

2 Claims, 3 Drawing Sheets

GAGAGAGAAACCAGAGAGTGAGCCGAGACAGCAAACATCAGATCG

TGCCCCGACCCACGCCAGC ATG GGC TCC TTC TCC ATC ACC AAG GGC TTC TTC CTC TTC
          Met Gly Ser Phe Ser Ile Thr Lys Gly Phe Phe Leu Phe
           1

CTG GCC TTT TGG CTC CCA GGC CAT ATT GGA GCA AAT CCC GTA TAC AGT GCG GTG
Leu Ala Phe Trp Leu Pro Gly His Ile Gly Ala Asn Pro Val Tyr Ser Ala Val
        20

TCC AAC ACA GAT CTG ATG GAT TTC AAG AAC CTG CTA GAC CAC CTG GAG GAG AAG
Ser Asn Thr Asp Leu Met Asp Phe Lys Asn Leu Leu Asp His Leu Glu Glu Lys
           40

ATG CCG GTA GAA GAT GAG GTC ATG CCT CCG CAG GCC CTG AGC GAG CAG ACC GAT
Met Pro Val Glu Asp Glu Val Met Pro Pro Gln Ala Leu Ser Glu Gln Thr Asp
             60

GAA GCG GGG GCG GCA CTT AGC TCC CTC TCT GAG GTG CCT CCC TGG ACT GGG GAA
Glu Ala Gly Ala Ala Leu Ser Ser Leu Ser Glu Val Pro Pro Trp Thr Gly Glu
               80

GTC AAC CCG TCT CAG AGA GAT GGA GGT GCT CTC GGG CGC GGC CCC TGG GAC CCC
Val Asn Pro Ser Gln Arg Asp Gly Gly Ala Leu Gly Arg Gly Pro Trp Asp Pro
                  100

TCC GAT AGA TCT GCC CTC TTG AAA AGC AAA CTG AGG GCT CTG CTC GCT GGC CCT
Ser Asp Arg Ser Ala Leu Leu Lys Ser Lys Leu Arg Ala Leu Leu Ala Gly Pro
                   120

CI
CGG AGC CTG CGA AGA TCA AGC TGC TTC GGG GGT AGG ATT GAC AGG ATT GGA GCC
Arg Ser Leu Arg Arg Ser Ser Cys Phe Gly Gly Arg Ile Asp Arg Ile Gly Ala

CAG AGC GGA CTA GGC TGC AAC AGC TTC CGG TAC CGA AGA TAA CAGCCAAATCTGCTC
Gln Ser Gly Leu Gly Cys Asn Ser Phe Arg Tyr Arg Arg
140                 152

GAGCAGATCGCAAAAGATCCCAAGCCCTTGCGGTGTGTCACACAGCTTGGTCGCATTGCCACTGAGAGGTG

GTGAATACCCTCCTGGAGCTGCAGCTTCCTGTCTTCATCTATCACGATCGATGTTAAGTGTAGATGAGTGG

TTTAGTGAGGCCTTACCTCTCCCACTCTGCATATTAAGGTAGATCCTCACCCCTTTCAGAAAGCAGTTGGA

AAAAAATAAATCCGAATAAACTTCAGCACCACGGAC

FIG. 3

ISOLATION, PURIFICATION AND SEQUENCE DETERMINATION OF CARDIONATRINS

CROSS REFERENCE TO RELATED APPLICATIONS

This application is a continuation of application Ser. No. 706,379, filed Feb. 27, 1985, now abandoned, which is a continuation-in-part of my earlier filed application Ser. No. 351,036 filed Feb. 22, 1982 now abandoned, a continuation in part thereof Ser. No. 473,442 filed Mar. 9, 1983 now abandoned and a second continuation in part Ser. No. 546,817 filed Oct. 31, 1983 now U.S. Pat. No. 4,663,437. This application is also related to U.S. patent application Ser. No. 626,219 filed June 29, 1984 by Peter L. Davies, the disclosures of all of which are incorporated herein by reference.

FIELD OF THE INVENTION

This invention relates to peptides which may be isolated from mammalian heart atria and which exhibit potent diuretic, natriuretic, vasodilatory and cardioinhibitory properties. They are also inhibitors of production and/or release of aldosterone and arginine vasopressin.

BACKGROUND OF THE INVENTION

It has been known for several years that the muscle cells of the atrial myocardium in mammals contain, in addition to contractile elements similar to those found in ventricular fibers, a highly developed Golgi complex, a relatively high proportion of rough endoplasmic reticulum, and numerous membrane-bound storage granules, referred to as specific atrial granules. No such granules appear to exist in ventricular muscle cells. Peptide isolates from the atrial granules have been shown to exhibit potent diuretic, natriuretic and vasodilatory properties. In my earlier application Ser. No. 473,442, a peptide defined by 28 amino acid residues was described and in my application Ser. No. 546,817 that peptide was defined as a 28 residue disulfide-looped structure and named Cardionatrin I. In commonly assigned application Ser. No. 626,219 filed June 29, 1984 by Peter L. Davies the sequence of a cloned cDNA for rat cardionatrin precursor has been established. The precursor, preprocardionatrin, has been shown to contain 152 amino acids and cardionatrin I containing a 28 amino acid sequence beginning at residue 123 thereof may be cleaved therefrom.

Others have verified the preprocardionatrin sequence and have reported a multitude of different peptides which differ from Cardionatrin I by a few amino acids more or less. In contrast, I have consistently observed only three other bio-active peptides, cardionatrins II, III and IV (as hereinafter defined) which have significantly larger molecular weights than Cardionatrin I, and which can be derived from a common precursor.

OBJECTS OF INVENTION

It is an object of the present invention to provide processes for the isolation and purification of specific bioactive peptides from rat atrial muscle.

It is another object of the present invention to provide a composition of matter comprising a peptide, in purified form, having diuretic and natriuretic activity and having an amino acid composition comprising: Asn, Pro, Val, Tyr, Ser, Ala, Val, Ser, Asn, Thr, Asp, Leu, Met, Asp, Phe, Lys, Asn, Leu, Leu, Asp, His, Leu, Glu, Glu, Lys, Met, Pro, Val, Glu, Asp, Glu, Val, Met, Pro, Pro, Gln, Ala, Leu, Ser, Glu, Gln, Thr, Asp, Glu, Ala, Gly, Ala, Ala, Leu, Ser, Ser, Leu, Ser, Glu, Val, Pro, Pro, Trp, Thr, Gly, Glu, Val, Asn, Pro, Ser, Gln, Arg, Asp, Gly, Gly, Ala, Leu, Gly, Arg, Gly, Pro, Trp, Asp, Pro, Ser, Asp, Arg, Ser, Ala, Leu, Leu, Lys, Ser, Lys, Leu, Arg, Ala, Leu, Leu, Ala, Gly, Pro, Arg, Ser, Leu, Arg, Arg, Ser, Ser, Cys, Phe, Gly, Gly, Arg, Ile, Asp, Arg, Ile, Gly, Ala, Gln, Ser, Gly, Leu, Gly, Cys, Asn, Ser, Phe, Arg, Tyr (hereinafter referred to as Cardionatrin IV)

It is yet another object of the present invention to provide a composition of matter comprising a peptide, in purified form, having diuretic and natriuretic activity and having an amino acid composition comprising Leu, Ser, Ser, Leu, Ser, Glu, Val, Pro, Pro, Trp, Thr, Gly, Glu, Val, Asn, Pro, Ser, Gln, Arg, Asp, Gly, Gly, Ala, Leu, Gly, Arg, Gly, Pro, Trp, Asp, Pro, Ser, Asp, Arg, Ser, Ala, Leu, Leu, Lys, Ser, Lys, Leu, Arg, Ala, Leu, Leu, Ala, Gly, Pro, Arg, Ser, Leu, Arg, Arg, Ser, Ser, Cys, Phe, Gly, Gly, Arg, Ile, Asp, Arg, Ile, Gly, Ala, Gln, Ser, Gly, Leu, Gly, Cys, Asn, Ser, Phe, Arg, Tyr (hereinafter referred to as Cardionatrin III.)

STATEMENT OF INVENTION

In satisfaction of the objects of this invention there is provided a process for the preparation of a purified bioactive peptide (Cardionatrin IV) having an amino acid sequence comprising: Asn, Pro, Val, Tyr, Ser, Ala, Val, Ser, Asn, Thr, Asp, Leu, Met, Asp, Phe, Lys, Asn, Leu, Leu, Asp, His, Leu, Glu, Glu, Lys, Met, Pro, Val, Glu, Asp, Glu, Val, Met, Pro, Pro, Gln, Ala, Leu, Ser, Glu, Gln, Thr, Asp, Glu, Ala, Gly, Ala, Ala, Leu, Ser, Ser, Leu, Ser, Glu, Val, Pro, Pro, Trp, Thr, Gly, Glu, Val, Asn, Pro, Ser, Gln, Arg, Asp, Gly, Gly, Ala, Leu, Gly, Arg, Gly, Pro, Trp, Asp, Pro, Ser, Asp, Arg, Ser, Ala, Leu, Leu, Lys, Ser, Lys, Leu, Arg, Ala, Leu, Leu, Ala, Gly, Pro, Arg, Ser, Leu, Arg, Arg, Ser, Ser, Cys, Phe, Gly, Gly, Arg, Ile, Asp, Arg, Ile, Gly, Ala, Gln, Ser, Gly, Leu, Gly, Cys, Asn, Ser, Phe, Arg, Tyr and a molecular weight of about 13,700 which comprises:

(a) extracting said Cardionatrin IV from rat atria using a strongly acid medium and (b) purifying said bioactive peptide (Cardionatrin IV composition) by adsorption on octadecylsylilsilica and a combination of high and low pressure liquid chromatography.

In further satisfaction there is provided a process for the preparation of a purified bioactive peptide (Cardionatrin III) having an amino acid sequence Leu, Ser, Ser, Leu, Ser, Glu, Val, Pro, Pro, Trp, Thr, Gly, Glu, Val, Asn, Pro, Ser, Gln, Arg, Asp, Gly, Gly, Ala, Leu, Gly, Arg, Gly, Pro, Trp, Asp, Pro, Ser, Asp, Arg, Ser, Ala, Leu, Leu, Lys, Ser, Lys, Leu, Arg, Ala, Leu, Leu, Ala, Gly, Pro, Arg, Ser, Leu, Arg, Arg, Ser, Ser, Cys, Phe, Gly, Gly, Arg, Ile, Asp, Arg, Ile, Gly, Ala, Gln, Ser, Gly, Leu, Gly, Cys, Asn, Ser, Phe, Arg, Tyr which comprises (a) extracting said Cardionatrin III from rat atria using a strongly acid medium; and (b) purifying said bioactive peptide (Cardionatrin III) composition by adsorption on octadecylsylilsilica, and a combination of high and low pressure liquid chromatography.

In still further satisfaction there is provided a purified bioactive composition containing a peptide having a molecular weight of about 13,700 and an amino acid sequence comprising Asn, Pro, Val, Tyr, Ser, Ala, Val, Ser, Asn, Thr, Asp, Leu, Met, Asp, Phe, Lys, Asn, Leu, Leu, Asp, His, Leu, Glu, Glu, Lys, Met, Pro, Val, Glu, Asp, Glu, Val, Met, Pro, Pro, Gln, Ala, Leu, Ser, Glu, Gln, Thr, Asp, Glu, Ala, Gly, Ala, Ala, Leu, Ser, Ser, Leu, Ser, Glu, Val, Pro, Pro, Trp, Thr, Gly, Glu, Val, Asn, Pro, Ser, Gln, Arg, Asp, Gly, Gly, Ala, Leu, Gly, Arg, Gly, Pro, Trp, Asp, Pro, Ser, Asp, Arg, Ser, Ala, Leu, Leu, Lys, Ser, Lys, Leu, Arg, Ala, Leu, Leu, Ala, Gly, Pro, Arg, Ser, Leu, Arg, Arg, Ser, Ser, Cys, Phe, Gly, Gly, Arg, Ile, Asp, Arg, Ile, Gly, Ala, Gln, Ser, Gly, Leu, Gly, Cys, Asn, Ser, Phe, Arg, Tyr. By yet another aspect there is provided a purified bioactive composition containing a peptide having a molecular weight of about 8,000 and an amino acid sequence comprising Leu, Ser, Ser, Leu, Ser, Glu, Val, Pro, Pro, Trp, Thr, Gly, Glu, Val, Asn, Pro, Ser, Gln, Arg, Asp, Gly, Gly, Ala, Leu, Gly, Arg, Gly, Pro, Trp, Asp, Pro, Ser, Asp, Arg, Ser, Ala, Leu, Leu, Lys, Ser, Lys, Leu, Arg, Ala, Leu, Leu, Ala, Gly, Pro, Arg, Ser, Leu, Arg, Arg, Ser, Ser, Cys, Phe, Gly, Gly, Arg, Ile, Asp, Arg, Ile, Gly, Ala, Gln, Ser, Gly, Leu, Gly, Cys, Asn, Ser, Phe, Arg, Tyr.

BRIEF DESCRIPTION OF DRAWINGS

FIG. 3 is a schematic diagram of preprocardionatrin and its cleavage products.

DETAILED DESCRIPTION OF PREFERRED EMBODIMENTS

Figure 1:
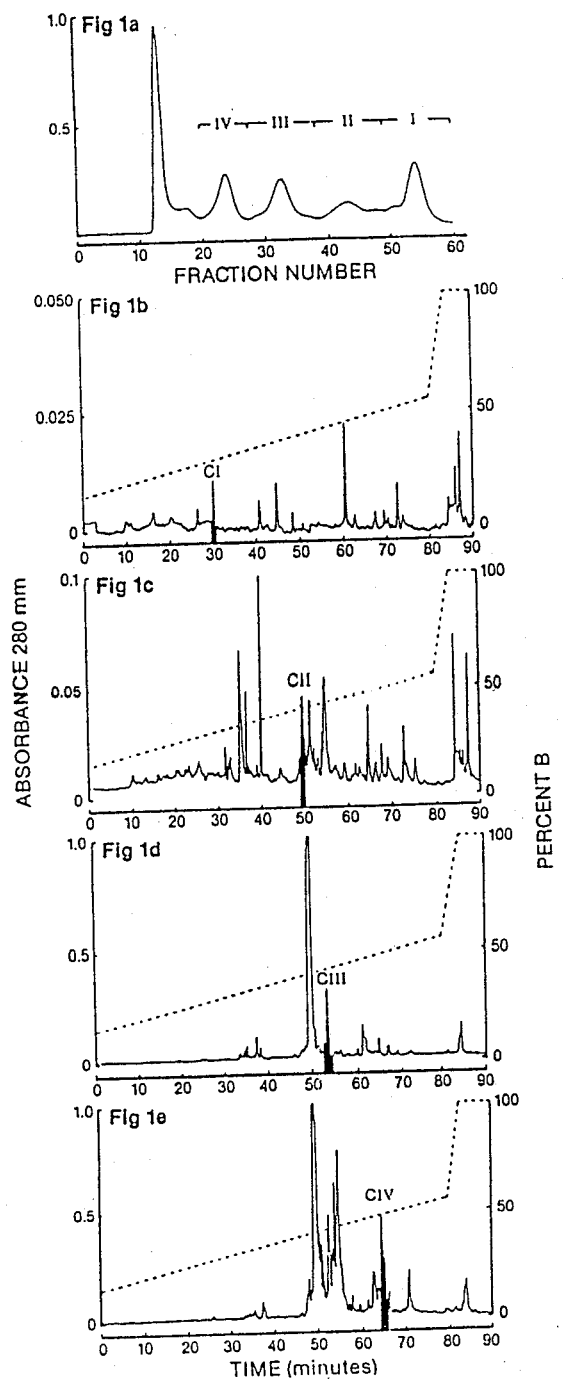
FIG. 1a is a graph illustrating gel permeation chromatography of atrial extracts
FIGS. 1b-1e are graphs illustrating purification of Cardionatrins I, II, III and IV respectively by HPLC.
Figure 2:
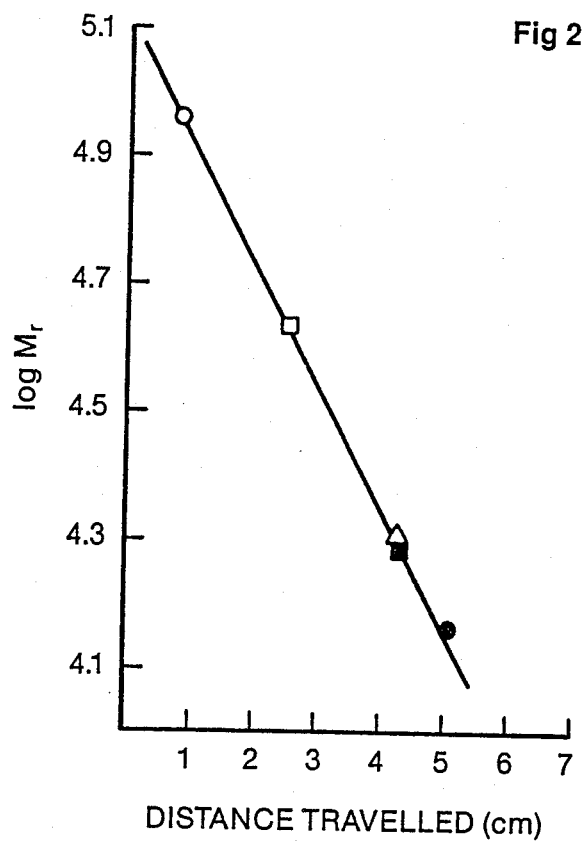
FIG. 2 is a graph illustrating SDS-urea-polyacrylamide gel electrophoresis of Cardionatrin IV

For the purposes of this application it has been established previously that all mammalian heart atria tested contain the specific granules referred to above and that neither the diet of the mammal nor the physical condition i.e. fresh, fresh-frozen or frozen, of the atria has any significant effect upon the extracted product. The peptide extract yield from different species may vary considerably but the composition of the extract for each species is remarkably consistent. There may be minor differences in amino acid composition between extracts from different species. Thus, as rat atria have been shown to contain a relatively high concentration of the cardionatric peptides (relative to beef, human and other mammalian atria), one thousand frozen rat atria from non-specific commercial sources were employed. The atria were ground together with solid carbon dioxide chips and homogenized in 10 volumes of a strongly acidic medium comprising (w/v) 1.0M acetic acid/1.0N HCl/1% NaCl using a Polytron ®. After centrifugation of the extracts, 20 ml aliquots of supernatants were passed through pre-wetted $C_{18}$ Sep-Pak ® (Waters) cartridges which contain octadecylsylilsilica. Each cartridge was washed with 20 ml of 0.1% trifluoracetic acid (TFA) and eluted with 3 ml of 80% acetonitrile in 0.1% TFA. The combined cartridge eluates were freeze-dried, then dissolved in 5 ml of 1.0M acetic acid/1% NaCl and fractionated on a Bio-Gel ® P-10 column (2.5×40 cm) equilibrated with the same solution. Fraction pools I, II, III and IV indicated in FIG. 1a were futher processed by high pressure liquid chromatography (HPLC) by directly pumping them into two serially connected Vydac ® $C_{18}$ columns (10×250 mm) pre-equilibrated with 12% acetonitrile in 0.1% TFA. Elution was carried out at 3.0 ml/min with acetonitrile gradients (12–44%) containing 0.1% TFA. These gradients were achieved by varying the input of the "organic" pump (%B, FIGS. 1b-e) which delivered an 80% (v/v) acetonitrile solution in 0.1% TFA. Elution times for cardionatrins I, II, III and IV were determined by the rat bioassay and are indicated in FIGS. 1b, 1c, 1d, 1e, as CI, CII, CIII and CIV respectively. Cardionatrins I and II were isolated as described in Biochem-Biophys Res. Comm 117, 859–865 (1983), and further purification in similar acetonitrile gradients but containing 0.13% heptafluorobutyric acid as counter ion. Cardionatrins III and IV were further purified by high performance cation exchange chromatography (Spherogel ® TSK, 4×300 mm, Altex) using a gradient over 60 minutes at 1.0 ml/min of 0.010M to 1.0M ammonium formate buffer, pH 6.5, containing 10% acetonitrile throughout. All cardionatrins went through a final purification step performed in a Vydac ® $C_{18}$ column (4.6×250 mm) eluted at 1.5 ml/min with acetonitrile gradients containing 0.1% TFA. SDS-ureapolyacrylamide gel electrophoresis for cardionatrin IV was performed using essentially the technique described by Laemmli in Nature 227, 680–685 (1970), as shown in FIG. 2. The molecular weights of standard proteins were (a) 92,500 (phosphorylase B); (b) 66,200 (bovine serum albumin; (c) 45,000 (ovalbumin; (d) 31,000 (carbonic anhydrase); (e) 21,500 (soybean trypsin inhibitor) and (f) lysozyme (14,300). The standard curve was constructed using ovalbumin (O), carbonic anhydrase (□), soybean trypsin inhibitor (△) and lysozyme (●). Cardionatrin IV is indicated by (■).

PREPROCARDIONATRIN AND ITS CLEAVAGE PRODUCTS

Poly(A)+RNA was isolated from rat atria as previously described in co-pending U.S. patent application No. 626,219 and used to prepare cDNA clones. In this instance the double-stranded cDNAs were G-tailed and annealed into the C-tailed Pst I site of pUC 9 which was then used to transform E. coli JM83 to ampicillin resistance. Colonies (650) which remained white in the presence of X-gal were screened for hybridization to the nick-translated P-labelled insert from the cardionatrin cDNA clone car 3. DNA from one of the eleven clones that hybridized (car 60) was end-labelled using the Klenow fragment of E. coli DNA polymerase I and sequenced from the Bgl II sites at 166 bp and 379 bp, the AWva Ii site at 367 bp, the Acc I site at 143 bp, the Xho I site at 536 bp, the Cla I site at 657 bp, and from the Hind III and Acc I sites in the multiple cloning site of pUC 9 flanking the cDNA insert. Two putative polyadenylation signals are underlined in FIG. 3. The n-terminal sequences of cardionatrins IV and III are indicated by arrows aligned to the preprocardionatrin sequence. These sequences were determined by automatic Edman degradation using an Applied Biosystems Gas-Phase 470A Sequencer and analyzing the phenylthiohydantoin amino acids.

Cardionatrin I was identical to that isolated and sequenced previously as described in copending U.S. application Ser. No. 546,817. Cardionatrin IV had a molecular weight of between 13,600 and 13,700 and more accurately 13,663 according to urea-SDS-polyacrylamide gel electrophoresis (FIG. 2). The primary structure of the first 30 residues of this peptide was determined by stepwise Edman degradation of the unmodified protein using a gas phase sequencer (Applied Biosystems, model 470A). The sequence was identical with residues 25-54 of the anticipated preproprotein sequence derived from a cloned cDNA sequence (FIG. 3). Both the molecular weight and NH2-terminal sequence of cardionatrin IV are consistent with it being procardionatrin, but the amino acid composition (Table 1 below) suggest that it lacks the two COOH-terminal arginine residues.

TABLE 1

Amino acid compositions of cardionatrins I, III and IV

| Amino Acid | CI | CIII | CIV |
| --- | --- | --- | --- |
| Asx | 2.19 (2) | 5.9 (6) | 13.3 (14) |
| Thr |  | 0.97 (1) | 3.5 (3) |
| Ser | 4.72 (5) | 11.6 (12) | 13.4 (15) |
| Glx | 1.39 (1) | 4.8 (4) | 11.3 (12) |
| Pro |  | 6.2 (6) | 9.6 (10) |
| Gly | 5.03 (5) | 10.7 (11) | 13.1 (12) |
| Ala | 1.32 (1) | 5.2 (5) | 8.7 (10) |
| ½Cys | 2.40 (2) | 2.3 (2) | 1.8 (2) |
| Val |  | 2.2 (2) | 5.9 (6) |
| Met |  |  | 1.7 (3) |
| Ile | 2.37 (2) | 2.4 (2) | 2.2 (2) |
| Leu | 2.16 (2) | 9.4 (2) | 15.2 (15) |
| Tyr | 1.37 (1) | 0.8 (1) | 2.6 (2) |
| Phe | 2.28 (2) | 2.8 (2) | 3.8 (3) |
| Lys |  | 1.7 (2) | 3.1 (4) |
| His |  |  | 0.7 (1) |
| Arg | 4.73 (5) | 9.5 (10) | 8.4 (10) |
| Total residues | 28 | 76 | 124 |

Results of a 24 hr hydrolysis in constant boiling 6NHCl and analysis on a Beckman 119c amino acid analyzer.
Values in parenthesis indicate residues found in sequence.
Totals for CIII and CIV do not include Trp.

The amino terminal sequence of cardionatrin IV beginning with asparagine is the predicted cleavage point for the removal of the signal sequence. The analogous position in the human natriuretic factor precursor was shown to be a cleavage point by the isolation and characterization of—ANP, which is the human analog of cardionatrin IV. A further point of interest is that NH-terminus of cardionatrin IV is in register with, and matches almost exactly, the NH-terminal sequence of cardiodilatin, a peptide with smooth muscle relaxant activity isolated from porcine atria. The two differences in sequence—Gly-Ser in positions 5 and 6 of cardiodilatin compared to Ser-Ala at the same positions in rat procardionatrin—reflect the conserved nature of this peptide in different species.

Both cardionatrin II and III are present in such small amounts in acid extracts of rat atria that it has not been possible to characterize them extensively. However, amino acid sequence determination of the first seventeen residues of cardionatrin III located the amino terminus of this molecule at residue 73 of the preproprotein. Cardionatrin III has a calculated molecular weight between about 8,000 and 8,500 or more accurately about 8,325. The small amounts of purified cardionatrin II thus far recovered from atrial extracts (approx. 100 pmol per 1000 atria) has precluded accurate sequencing of this peptide. Since all four cardionatrins are natriuretic it is expected that they contain most of the sequence of cardionatrin I. Compositional analysis of cardionatrins III and IV (Table I above) indicated that these proteins extend up to and include tyrosine 150.

Identification of the start points for cardionatrin I and III in procardionatrin confirms that these products are derived from a common precursor, cardionatrin IV.

In independently establishing the nucleotide sequence of a cardionatrin complementary DNA clone 650 atrial cDNA clones were screened with a 250 bp cardionatrin cDNA probe corresponding nucleotide residues 334 to 582 in FIG. 3. Eleven clones hybridized to the probe. Their cDNA inserts were released by digestion with Bam HI and Eco RI and compared for size. Three inserts were close to full-length, based on previous estimates for the size of cardionatrin mRNA and, one of these, car 60, was sequenced (FIG. 3). the cDNA sequence, excluding the poly(a) tract and homopolymeric tracts, is 787 bp long, including 456 bp coding for the 152 residue cardionatrin preproprotein, and 64 bp and 267 bp for the 5' and 3' untranslated regions, respectively.

I claim:

1. A purified bioactive composition containing a peptide having a molecular weight of about 13,700 and an amino acid sequence comprising: Asn-Pro-Val-Tyr-Ser-Ala-Val-Ser-Asn-Thr-Asp-Leu-Met-Asp-Phe-Lys-Asn-Leu-Leu-Asp-His-Leu-Glu-Glu-Lys-Met-Pro-Val-Glu-Asp-Glu-Val-Met-Pro-Pro-Gln-Ala-Leu-Ser-Glu-Gln-Thr-Asp-Glu-Ala-Gly-Ala-Ala-Leu-Ser-Ser-Leu-Ser-Glu-Val-Pro-Pro-Trp-Thr-Gly-Glu-Val-A n-Pro-Ser-Gln-Arg-Asp-Gly-Gly-Ala-Leu-Gly-Arg-Gly-Pro-Trp-Asp-Pro-Ser-Asp-Arg-Ser-Ala-Leu-Leu-Lys-Ser-Lys-Leu-Arg-Ala-Leu-Leu-Ala-Gly-Pro-Arg-Ser-Leu-Arg-Arg-Ser-Ser-Cys-Phe-Gly-Gly-Arg-Ile-Asp-Arg-Ile-Gly-Ala-Gln-Ser-Gly-Leu-Gly-Cys-Asn-Ser-Phe-Arg- yr.

2. A purified bioactive composition containing a peptide having a molecular weight of about 8,000 and an amino acid sequence comprising Leu-Ser-Ser-Leu-Ser-Glu-Val-Pro-Pro-Trp-Thr-Gly-Glu-Val-Asn-Pro-Ser-Gln-Arg-Asp-Gly-Gly-Ala-Leu-Gly-Arg-Gly-Pro-Trp-Asp-Pro-Ser-Asp-Arg-Ser-Ala-Leu-Leu-Lys-Ser-Lys-Leu-Arg-Ala-Leu-Leu-Ala-Gly-Pro-Arg-Ser-Leu-Arg-Arg-Ser-Ser-Cys-Phe-Gly-Gly-Arg-Ile-A p-Arg-Ile-Gly-Ala-Gln-Ser-Glu-Leu-Gly-Cys-Asn-Ser-Phe-Arg-Tyr.

* * * * *